(12) United States Patent
Deghenghi

(10) Patent No.: US 7,034,050 B2
(45) Date of Patent: Apr. 25, 2006

(54) PSEUDOPEPTIDES GROWTH HORMONE SECRETAGOGUES

(76) Inventor: Romano Deghenghi, Romano Deghenghi, Chesaux Dessus B1, 1264-St-Cergue (CH)

( * ) Notice: Subject to any disclaimer, the term of this patent is extended or adjusted under 35 U.S.C. 154(b) by 209 days.

(21) Appl. No.: 10/835,563

(22) Filed: Apr. 28, 2004

(65) Prior Publication Data

US 2005/0245457 A1 Nov. 3, 2005

(51) Int. Cl.
*A61K 31/405* (2006.01)
*C07D 209/04* (2006.01)

(52) U.S. Cl. .................. 514/419; 514/414; 514/415; 548/455

(58) Field of Classification Search .......... 514/414, 514/415, 419; 548/455
See application file for complete search history.

(56) References Cited

U.S. PATENT DOCUMENTS

2002/0165343 A1* 11/2002 Martinez et al. ........... 530/331

* cited by examiner

*Primary Examiner*—Kamal A. Saeed
*Assistant Examiner*—Michael P. Barker

(74) *Attorney, Agent, or Firm*—Winston & Strawn LLP

(57) ABSTRACT

The present invention relates to novel growth hormone releasing pseudopeptides capable of stimulating the release of growth hormone from the pituitary and of promoting growth in mammals. The invention also provides pharmaceutical compositions comprising the pseudopeptides growth hormone secretagogues and a method for promoting the release of growth hormone in mammals. If continuously administered, the present pseudopeptides may also inhibit the release of growth hormone by down-regulating the growth response. An exemplary pseudopeptide compound of this invention is Aib-D-Trp-D-Trpψ[$CH_2$—NH—O]Gly-$NH_2$:

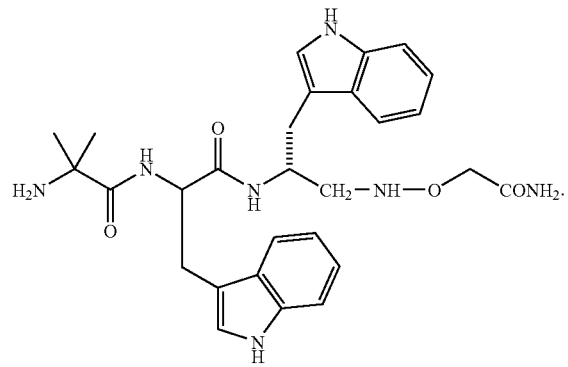

12 Claims, 1 Drawing Sheet

PSEUDOPEPTIDES GROWTH HORMONE SECRETAGOGUES

FIELD OF THE INVENTION

The present invention relates to pseudopeptide growth hormone secretagogues which are capable of causing the release of growth hormone from the pituitary, and to pharmaceutical formulations thereof. The present invention also relates to a method of treatment for promoting the release of growth hormone by administering the growth hormone releasing pseudopeptides to a subject in need of such treatment.

BACKGROUND OF THE INVENTION

The pituitary gland secretes growth hormone (GH) which stimulates growth in body tissues capable of growing and affects metabolic processes by increasing the rate of protein synthesis and decreasing the rate of carbohydrate synthesis in cells. Growth hormone also facilitates the mobilization and use of free fatty acids for energy.

Growth hormone secretion is regulated by two hypothalamic peptides: GH-releasing hormone (GHRH), which exerts a stimulatory effect on GH release, and somatostatin, which exhibits an inhibitory influence. Growth hormone levels can be increased by administering compounds known to induce GH release, such as GHRH. Administration of such growth hormone releasing agents and the resulting increase in the GH level provide important medical and physiological benefits in mammals, including the acceleration of growth, increase of muscular mass, and, with sufficiently high GH levels, enhanced production of milk.

It has been demonstrated that GH secretion can also be stimulated by synthetic oligopeptides termed GH-releasing peptides (GHRP), such as hexarelin and various hexarelin analogs (Ghigo et al., *European Journal of Endocrinology*, 136, 445–460, 1997). These compounds act through a mechanism which is distinct from that of GHRH (C. Y. Bowers, in "Xenobiotic Growth Hormone Secretagogues", B. Bercu and R. F. Walker, eds., pp. 9–28, Springer-Verlag, New York 1996) and by interaction with specific receptors localized in the hypothalamus and pituitary gland (G. Muccioli et al., *Journal of Endocrinology*, 157, 99–106, 1998; G. Muccioli, "Tissue Distribution of GHRP Receptors in Humans", Abstracts IV European Congress of Endocrinology, Sevilla, Spain, 1998).

Given the importance of growth hormone releasing peptides in veterinary and human medicine as in many commercial applications, there remains a need for growth hormone releasing peptides that are more efficacious than those currently in existence. The present invention addresses this need by providing growth hormone releasing pseudopeptides that are surprisingly found to more effectively stimulate the release of growth hormone than the known GH secretagogues.

SUMMARY OF THE INVENTION

The present invention provides novel pseudopeptides growth hormone secretagogues of formula I and II:

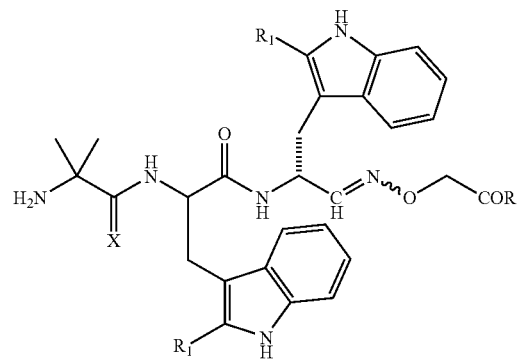

(I)

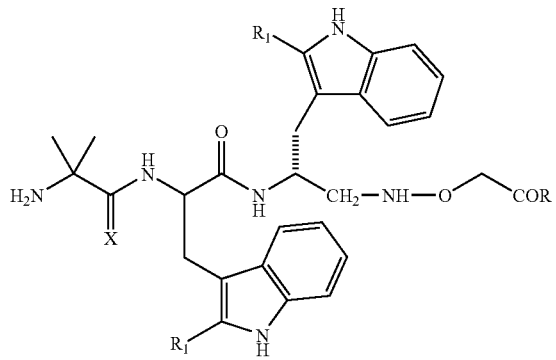

(II)

where R is OH, $NH_2$ or $NH-R_2$;
$R_1$ is H or $CH_3$;
$R_2$ is H or a lower alkyl of one to five carbon atoms; and
X is O or $H_2$.

The "~" sign in formula I denotes a E-(trans) or Z-(cis) isomer or a mixture of the two isomers.

When R is $NH_2$, $R_1$ and $R_2$ are H, and X is O in formulae I and II, the present invention provides the pseudopeptides of formula (Ia) and formula (IIa):

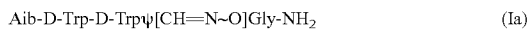

Aib-D-Trp-D-Trpψ[CH=N~O]Gly-NH$_2$ (Ia)

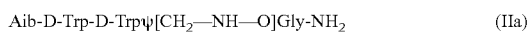

Aib-D-Trp-D-Trpψ[CH$_2$—NH—O]Gly-NH$_2$ (IIa)

where Aib is aminoisobutyric acid;
D-Trp is dextrotryptophan;
Gly is glycine; and
ψ designates pseudo.

The present pseudopeptides have been shown to be remarkably potent as growth hormone secretagogues both in vitro and in vivo, and can be used in pharmaceutical compositions in admixture with a pharmaceutically acceptable carrier or excipient. The pseudopeptide may be present in the composition as a pharmaceutically acceptable salt thereof, and the pharmaceutical composition may be prepared in a form suitable for parental, intranasal, subcutaneous or oral administration. The composition may be provided in a controlled release dosage form, for example as a subcutaneous implant made with a biodegradable polymer matrix as carrier.

The invention also provides a method for promoting the release of growth hormone in an animal by administering the pseudopeptides growth hormone secretagogues to a subject in need of growth hormone increase. Advantageously, the pseudopeptides may be administered subcutaneously or intravenously in an amount of about 0.1 µg to about 10 µg of total peptide per kg of body weight, or orally in an amount of about 30 µg to about 1000 µg of total peptide per kg of body weight.

The present invention also provides a method for inhibiting the release of growth hormone in an animal by continuously administering the pseudopeptides for an extended period of time and therefore down-regulating the animal's hormone response. This enables the peptides to effectively act as antagonists to growth hormone compounds such as Ghrelin.

DETAILED DESCRIPTION OF THE PREFERRED EMBODIMENTS

Figure 1:
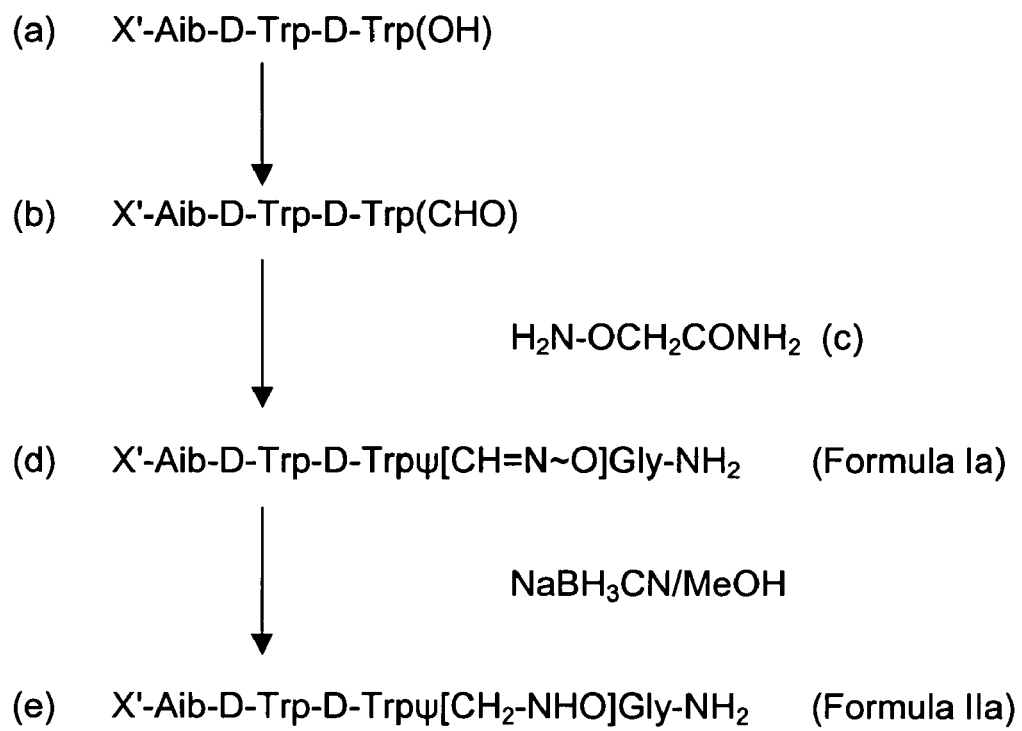
FIG. 1 schematically illustrates the steps of preparing pseudopeptides growth hormone secretagogues according to the present invention.

The present invention relates to novel growth hormone releasing pseudopeptides that are capable of causing the release of growth hormone from the pituitary and thereby promoting growth in mammals and providing numerous important benefits, such as increased muscular and bone mass and enhanced milk production. If administered continuously, the present pseudopeptides may also be used to inhibit the release of growth hormone by down-regulating the growth response.

The following definitions apply to the terms used throughout this specification, unless otherwise limited in specific instances. Aib denotes aminoisobutyryl, Boc is tertiary butyloxycarbonyl, Fmoc is 9-fluorenyl methoxycarbonyl, and Z is benzyloxycarbonyl. Trp and Gly are, respectively, the amino acids tryptophan and glycine. The notation "D-" is used to designate the dextro enantiomer, and the amino acid immediately following the "D-" notation has the D-configuration.

The term "lower alkyl" includes both straight and branched chain hydrocarbons, containing 1 to 40 carbons, preferably 1 to 20 carbons, more preferably 1 to 6 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 3 substituents including alkyl, aryl, alkenyl, alkynyl, hydroxy, arylalkyl, cycloalkyl, cycloalkylalkyl, alkoxy, arylalkyloxy, alkanoyl, amino, haloaryl, $CF_3$, $OCF_3$, aryloxy, heteroaryl, cycloalkylalkoxyalkyl, or cycloheteroalkyl.

As used herein, "therapeutically effective" means an amount or dose which, when administered to the animal, including human, patient or subject, renders a benefit or an effect of increasing the level of cellular proteins such as hormones, or renders a benefit or an effect of treating or preventing an abnormal biological condition or disease.

The present invention provides pseudopeptides that are capable of stimulating the release of GH from the pituitary of mammals. In particular, the present invention relates to the novel pseudopeptides GH secretagogues represented by the formula I and formula II:

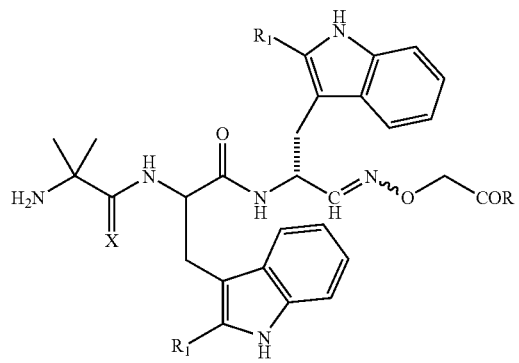

where R is OH, $NH_2$ or $NH—R_2$;
$R_1$ is H or $CH_3$;
$R_2$ is H or lower alkyl; and
X is O or $H_2$.

The "~" sign in formula I represents that it can be a trans (E) or cis (Z) isomer or a mixture of the two isomers.

In a preferred embodiment, the compound according to formula I may be formed such that R=$NH_2$, $R_1$=H, $R_2$=H, X=O and "~"=E/Z isomers, resulting in the following compound (Ia):

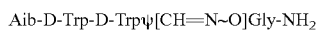

Aib-D-Trp-D-Trpψ[CH=N~O]Gly-$NH_2$ where Aib is aminoisobutyric acid;
D-Trp is dextrotryptophan;
Gly is glycine; and
ψ denotes pseudo.

Similarly, where R=$NH_2$, $R_1$=H, $R_2$=H, and X=O in formula II, formula II represents the following compound (IIa):

Aib-D-Trp-D-Trpψ[$CH_2$—NH—O]Gly-$NH_2$ where Aib is aminoisobutyric acid;
D-Trp is dextrotryptophan;
Gly is glycine; and
ψ denotes pseudo.

The compounds of the present invention may be prepared according to the following general synthetic scheme, as well as the usual methods of peptide chemistry known in the art. The following synthetic scheme provides exemplary reagents and procedures for the reactions.

Referring to FIG. 1, the protected tripeptide (a) is obtained by the classical solid phase synthesis and transformed into the aldehyde (b) by conventional methods (see, e.g., R. Vanderesse et al., *J. Peptide Sci.* 2, 282–299 (2003)). X' represents a protecting group, preferably chosen from Boc, Fmoc, and Z. The solid-phase synthesis starts from the C-terminal end of the compound. A suitable starting material can be prepared, for example, by attaching the required protected α-amino acid to a chloromethylated resin, a hydroxymethylated resin, a benzhydrylamine resin (BHA), or to a para-methyl-benzhydrylamine resin (p-Me-BHA). As an example, a chloromethylated resin may be BIOBEADS SX1, produced by BioRad Laboratories in Richmond, Calif. The preparation of the hydroxymethylated resin is described by Bodansky et al., *Chem. Ind.* 38, 15997 (London, 1966). The BHA resin is described in Pietta and Marshall, Chem. Comm., 650 (1970), and is commercially available from Peninsula Laboratories Inc. in Belmont, Calif.

The aldehyde (b) in FIG. 1 is then coupled with aminoxyacetamide (c), commercially available from Neosystem, 67100-Strasbourg, France, to produce the aldoxime (d) as a mixture of E/Z isomers. The aldoxime (d) is then deprotected to give the pseudopeptide of formula (Ia). The protecting group can be removed by means of different acid reagents, such as trifluoroacetic acid (TFA) or hydrochloric acid (HCl) dissolved in organic solvents at room temperature.

Alternatively, the aldoxime (d) may be further reduced with $NaBH_3CN$ in MeOH or AcOH to produce the amidoxypeptide (e). Deprotecting the amidoxypeptide (e) yields the pseudopeptide of formula (IIa). Final purification of the compounds can be obtained by silica gel chromatography.

The compounds (Ia) and (IIa) have a binding affinity to human pituitary gland tissues and have been shown to be remarkably potent as GH secretagogues both in vitro and in vivo. Their binding affinity is comparable to that of the natural ligand ghrelin and superior to the binding affinity of the synthetic GH secretagogues such as hexarelin, MK 0677, a non-peptidyl GHRP mimetic that binds to pituitary GHRP receptors, and JMV 1843. Similarly, the present compounds have a binding affinity to rat epididynial adipocytes that is comparable to that of rat ghrelin and superior to that of MK 0677 and hexarelin. Significantly, both compounds (Ia) and (IIa) are observed to be remarkably potent in stimulating the GH release both in vitro and in vivo. For example, when neonatal rats were injected subcutaneously with the present pseudopeptides (Ia) and (IIa), the amount of growth hormone released in the rats exceeded the amount released when the standard GH secretagogues MK 0677 and hexarelin were administered.

Therefore, the present pseudopeptides can be advantageously used in compositions designed to release growth hormone in an animal, including a human. For instance, the pseudopeptides can be administered to commercially important animals such as swine, cattle, and sheep to accelerate their growth and to increase their milk production.

Furthermore, the present pseudopeptides growth hormone secretagogues and their phamaceutically acceptable salts may be used as an active ingredient in pharmaceutical compositions. Pharmaceutically acceptable salts of the present pseudopeptides include but are not limited to organic or inorganic addition salts such as trifluoroacetate, pamoate, hydrochloride, hydrobromide, phosphate, sulfate, acetate, succinate, ascorbate, tartrate, gluconate, benzoate, malate and fumarate salts. If desired, the present pharmaceutical compositions may also include another pharmaceutically active material such as an antibiotic.

The present pharmaceutical compositions may optionally comprise a pharmaceutical carrier, excipient, vehicle, diluent, matrix or delayed release coating. Examples of such carriers, excipients, vehicles and diluents can be found in Remington's Pharmaceutical Sciences, Eighteenth Edition (A. R. Gennaro, Ed., Mack Publishing Company, Easton, Pa., 1990), and examples of delayed release pharmaceutical forms, comprising biodegradable matrices suitable for subcutaneous implant, are described in WO 92/22600 and WO 95/12629. Hence, compositions comprising the pseudopeptides of the present invention can be administered to animals, including humans, through various means, including parenteral or oral administration and subcutaneous injection. They may also be formulated in controlled release systems, such as biodegradable microcapsules, microspheres, or subcutaneous implants.

The therapeutically effective dose of the present compositions can vary according to the specie, age, sex and weight of the treated patient or subject, but can be easily determined by one skilled in the art. For example, when intravenously administered in humans, the preferred dose falls in the range from about 0.1 μg to about 10 μg of total peptide per kg of body weight. When orally administered, higher amounts are typically necessary, and the dosage level for oral administration in humans is typically from about 30 μg to about 1000 μg of polypeptide per kg of body weight. The exact level can be easily determined empirically based on the above disclosure.

As is well known in the art, the known and potential uses of growth hormone are varied and multitudinous. Therefore, the administration of the present pseudopeptides and pharmaceutical compositions comprising the present pseudopeptides can have the same effects and benefits as administering growth hormone itself, including: stimulation of growth hormone release and maintenance of muscle strength in elderly humans; stimulation and increase of muscle mass and muscle strength; stimulation of the immune system; acceleration of wound healing and bone fracture repair; treatment of osteoporosis; treatment of growth deficiency in children; treatment of growth retardation associated with genetic disorders; treatment of obesity; prevention of catabolic side effects of glucocorticoids; and alleviation of numerous other health conditions associated with growth hormone deficiency. Given the importance of growth hormone in animals and humans, the present pseudopeptides growth hormone secretagogues can be utilized in various commercial and medical applications to provide a convenient and effectively way of stimulating growth hormone release.

In addition, if these pseudopeptides are continuously administered to a mammal or human for an extended period of time, it is possible to down-regulating the animal's hormone response. This enables the peptides to effectively act as antagonists to growth hormone compounds.

In this regard, it has been observed that these agents work through a GHR (Growth Hormone Receptor) discovered by Merck. The natural ligand (hormone) was discovered by a Japanese team and is called Ghrelin. (See, Muccioli, G. et al. Eur. J. Pharmacol., 440, 235–254, 2002). Ghrelin is a 28 amino acid octanoylated peptide which is difficult to develop into a drug due to the side effects it causes, particularly in elderly patients. Ghrelin not only liberates Growth Hormone, but stimulates appetite and is involved in causing obesity. It addition to mimicking Ghrelin, it is possible to antagonize its effects by downregulating its receptor. This can be done by frequent or continuous stimulation of these pseudopeptides, similar to what was done with GnRH (LHRH) agonists, which are known to become antagonists after continuous administration, such as by an implant or by subcutaneous injection on a daily basis for a month, or by injection of a delayed release formulation. In other words, growth can be achieved by acute administration of these pseudopeptides, but it is also possible to antagonize some of the Ghrelin actions (e.g., appetite stimulation and obesity) if these pseudopeptides are administered frequently or continuously in the manners previously mentioned. This demonstrates the flexibility and usefulness of the pseudopeptides of the present invention.

What is claimed is:

1. A pseudopeptide compound of formula (I) or formula (II):

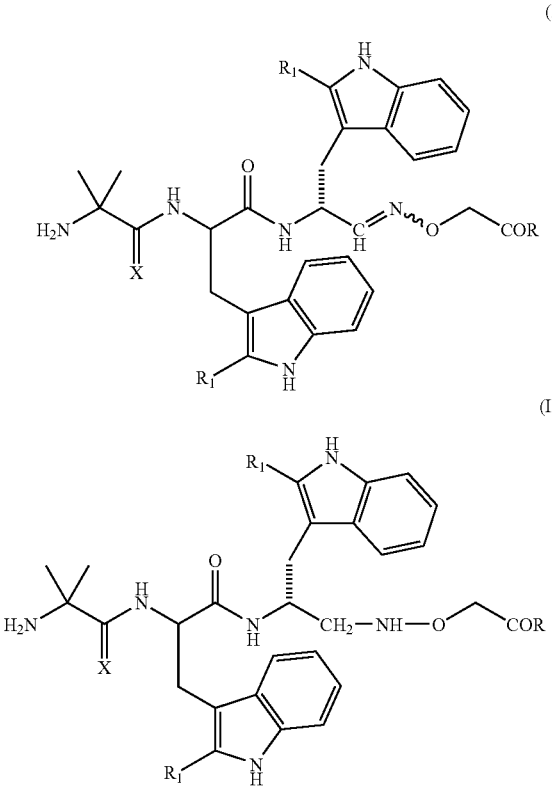

or a pharmaceutically acceptable salt thereof, wherein:

R is OH, $NH_2$ or $NH-R_2$;

$R_1$ is hydrogen or $CH_3$;

$R_2$ is hydrogen or lower alkyl; and

X is O or two singly bonded hydrogen atoms.

2. The compound according to claim 1 wherein R is $NH_2$, $R_1$ and $R_2$ are hydrogen, and X is oxygen.

3. A pseudopeptide having the formula (Ia):

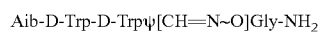

wherein Aib is aminoisobutyric acid;

D-Trp is dextrotryptophan;

Gly is glycine; and

ψ is pseudo.

4. A pseudopeptide having the formula (IIa):

wherein Aib is aminoisobutyric acid;

D-Trp is dextrotryptophan;

Gly is glycine; and

ψ is pseudo.

5. A pharmaceutical composition comprising a pseudopeptide compound of claim 1 as active ingredient and a pharmaceutically acceptable carrier or excipient.

6. The pharmaceutical composition according to claim 5 wherein the pseudopeptide compound is in the form of a pharmaceutically acceptable addition salt and the composition is in a form suitable for parenteral, intranasal, subcutaneous or oral administration.

7. The pharmaceutical composition according to claim 5 wherein the carrier is a biodegradable polymer matrix so that the composition is in a controlled release dosage form.

8. The pharmaceutical composition according to claim 7 wherein the controlled release dosage form is a subcutaneous implant.

9. A method for promoting the release of growth hormone in an animal which comprises administering the compound of claim 1 to a subject in need of such treatment.

10. The method according to claim 9 wherein the pseudopeptide compound is administered subcutaneously or intravenously in an amount of about 0.1 μg to about 10 μg of total peptide per kg of body weight.

11. The method according to claim 9 wherein the pseudopeptide compound is administered orally in an amount of about 30 μg to about 1000 μg of total peptide per kg of body weight.

12. A method for inhibiting the release of growth hormone in an animal by continuously administering the compound of claim 1 for an extended period of time and thereby downregulating the animal's hormone response.

* * * * *